(12) United States Patent
Mitsuishi et al.

(10) Patent No.: US 7,819,894 B2
(45) Date of Patent: Oct. 26, 2010

(54) MANIPULATOR WITH MULTIPLE DEGREES OF FREEDOM

(75) Inventors: Mamoru Mitsuishi, Tokyo (JP); Shinichi Warisawa, Tokyo (JP); Jumpei Arata, Kasugai (JP); Toji Nakazawa, Tokyo (JP)

(73) Assignees: Mamoru Mitsuishi, Tokyo (JP); THK Co., Ltd., Tokyo (JP)

( * ) Notice: Subject to any disclaimer, the term of this patent is extended or adjusted under 35 U.S.C. 154(b) by 802 days.

(21) Appl. No.: 10/582,885

(22) PCT Filed: Dec. 14, 2004

(86) PCT No.: PCT/JP2004/018654

§ 371 (c)(1),
(2), (4) Date: Jun. 8, 2007

(87) PCT Pub. No.: WO2005/055840

PCT Pub. Date: Jun. 23, 2005

(65) Prior Publication Data

US 2008/0039892 A1    Feb. 14, 2008

(30) Foreign Application Priority Data

Dec. 15, 2003  (JP) ............................. 2003-417123

(51) Int. Cl.
*A61B 17/00* (2006.01)
(52) U.S. Cl. .................................................. 606/208
(58) Field of Classification Search . 74/490.01–490.15; 294/106, 115; 901/30–39; 414/729, 739; 606/205, 207, 208
See application file for complete search history.

(56) References Cited

U.S. PATENT DOCUMENTS 6,592,572 B1    7/2003  Suzuta (Continued)

FOREIGN PATENT DOCUMENTS

JP    60-009676 A    1/1985

(Continued)

OTHER PUBLICATIONS

International Search Report mailed Mar. 29, 2005 of International Application PCT/JP2004/018654.

(Continued)

*Primary Examiner*—Todd E Manahan
*Assistant Examiner*—Christopher Schubert
(74) *Attorney, Agent, or Firm*—Westerman, Hattori, Daniels & Adrian, LLP

(57) ABSTRACT

A bending forceps 1 has at least three degrees of freedom including relative opening/closing of a pair of gripping members 11a, 11b, rotation of both the gripping members around a first axis 15 and rotation of both the gripping members around a second axis 42 existing on an imaginary plane substantially perpendicular to the first axis 15. A drive power from an actuator is converted to each motion of the opening/closing of the gripping members, rotation thereof around the first axis and rotation thereof around the second axis by first to third link mechanisms 5, 6 and 7. The present invention enables the durability and control accuracy to be raised by employing a link mechanism as a drive power transmitting means. Further, the present invention facilitates sterilization, cleaning and attachment/detachment to/from a driving means.

4 Claims, 7 Drawing Sheets

U.S. PATENT DOCUMENTS

| | | |
|---|---|---|
| 6,889,116 B2 * | 5/2005 | Jinno .................. 700/245 |
| 2002/0055758 A1 | 5/2002 | Sasaki |
| 2003/0158576 A1 * | 8/2003 | Nagase et al. ........... 606/205 |

FOREIGN PATENT DOCUMENTS

| | | |
|---|---|---|
| JP | 06-311984 A | 11/1994 |
| JP | 2001-71290 A | 3/2001 |
| JP | 2001-145635 A | 5/2001 |
| JP | 2001-299768 A | 10/2001 |

OTHER PUBLICATIONS

International Preliminary Report on patentability dated Aug. 22, 2006, issued in corresponding PCT/JP2004/018654.

Japanese Office Action dated Nov. 10, 2009, issued in corresponding Japanese patent application No. 2003-41723.

* cited by examiner

FIG. 5
(b)
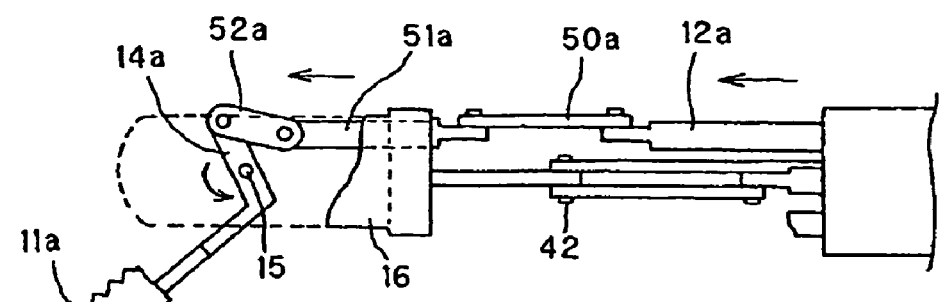
(a)
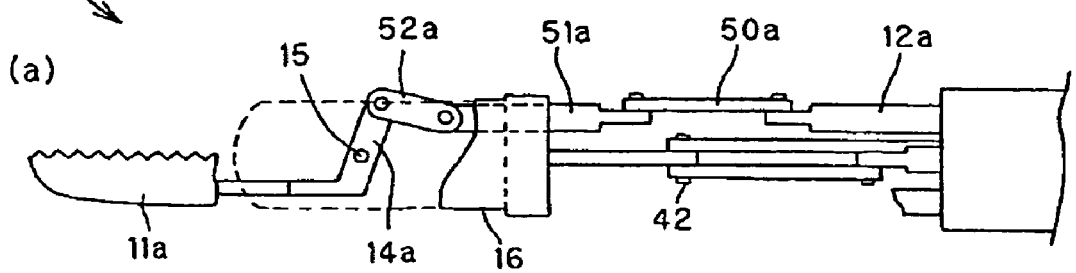
(c)
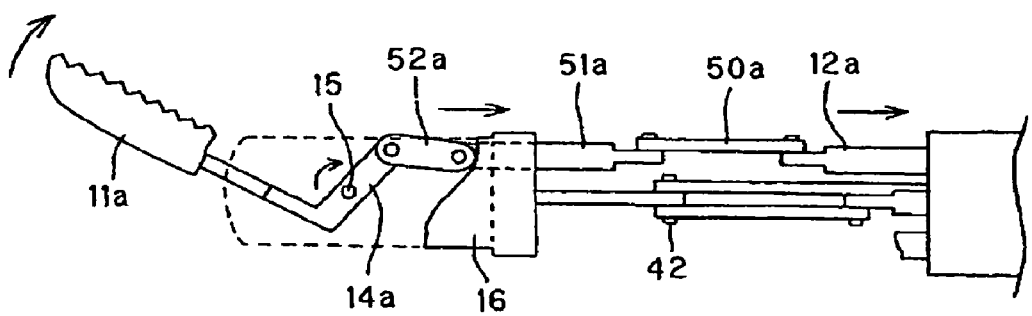

FIG. 6
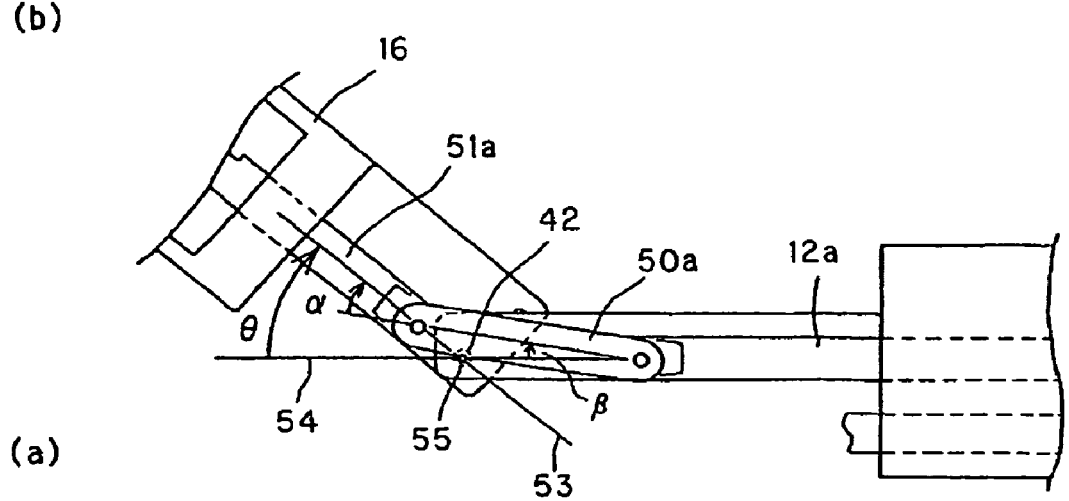
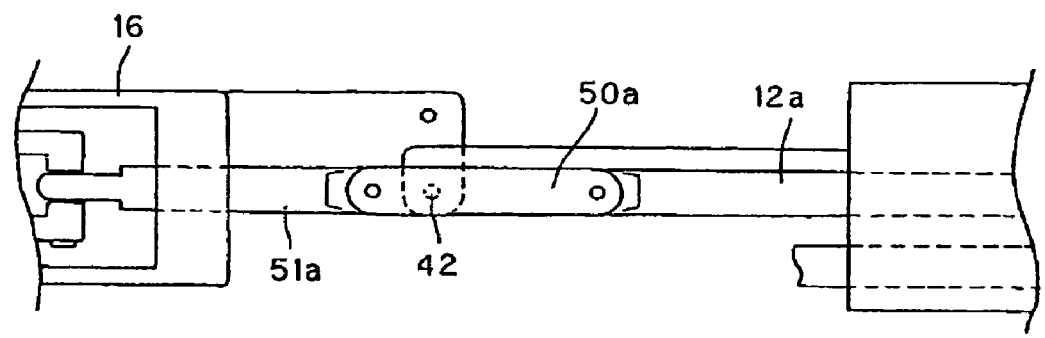
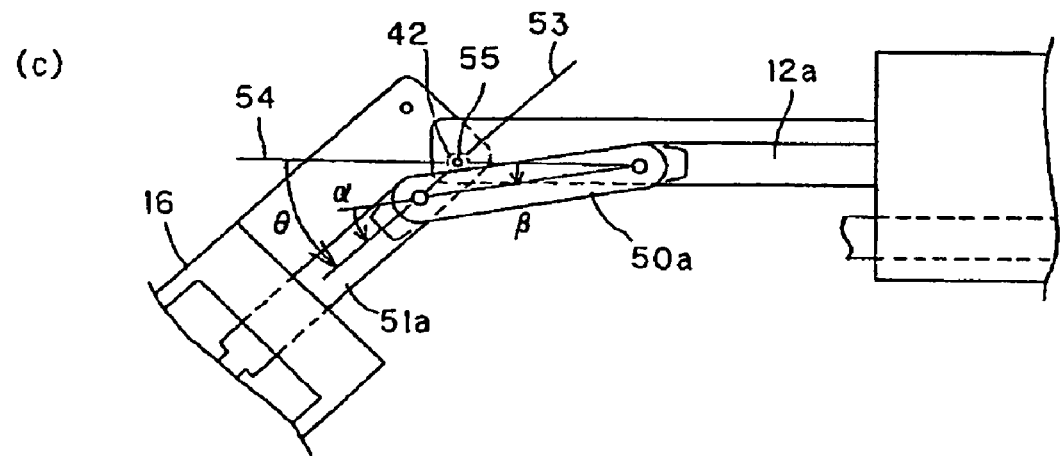

MANIPULATOR WITH MULTIPLE DEGREES OF FREEDOM

TECHNICAL FIELD

The present invention relates to a manipulator with multiple degrees of freedom for surgery used for abdominal cavity surgery and the like.

BACKGROUND ART

In recent years, attention has been paid to minimally invasive surgery represented by abdominal cavity surgery as a method of surgical operation. In the minimally invasive surgery, a surgical instrument such as an endoscope and forceps is inserted through an incised hole about 10 mm made in the surface of the body so as to carry out surgery inside the body. Therefore, this has such an advantage that it can reduce a damage to a patient or a possibility of giving a damage to the patient as compared with ordinary surgical operation.

The forceps used in the minimally invasive surgery does not allow an approach to a diseased part but from a limited direction because its posture is restricted by the incised hole. To execute operations such as gripping, ligation under such a condition simply, bending forceps (manipulator with multiple degrees of freedom), the front end portion of which is bent in multiple directions, have been developed aggressively.

As preceding technology about this kind of the manipulator with multiple degrees of freedom, for example, non-patent documents 1 to 3 can be mentioned. As a specific product, "da Vinci surgical system" manufactured by Intuitive Surgical, Inc. has been well known (refer to non-patent document 4).

Non-patent document 1: T. Oura and other 10 persons, "DEVELOPMENT OF FORCEPS MANIPULATOR SYSTEM FOR LAPAROSCOPIC SURGERY", JSME [No. 01-4] Robotics and Mechatronics lecture meeting '01 papers, 2A1-D8, 2001

Non-patent document 2: K. Ikuta and other three persons, "RESEARCH ON HYPER-FINGER FOR TELESURGERY OF ABDOMINAL CAVITY", JSME [No. 00-2] Robotics and Mechatronics lecture meeting '00 paper, 2P1-13-019, 2000

Non-patent document 3: Jeff M. Wndlandt and S. Shankar Sastry, "DESIGN AND CONTROL OF A SIMPLIFIED STEWART PLATFORM FOR ENDOSCOPY", Proceedings of the $33^{rd}$ Conference on Decision and Control Lake Buena Vista, Fla.-December 1994, pp. 357-362, 1994

Non-patent document 4: Gary S. Guthart and J. Kenneth Salisbury, Jr., "THE INTUITIVE™ TELESURGERY SYSTEM: OVERVIEW AND APPLICATION", Proceedings of the 2000 IEEE International Conference on Robotics & Automation San Francisco, Calif. April 2000, pp. 618-621, 2000

A conventional manipulator with multiple degrees of freedom employs wire as a drive power transmitting means from a drive unit. Bending of an articulation and opening/closing of the gripping portion are achieved by winding up wire with a drive unit.

However, driving with wire has following problems.

First, wire needs to be replaced frequently because it can be elongated or broken (for example, in the aforementioned "da Vince" system, replacement of wire is required for about 10 times of surgery) Further, it takes a considerable amount of labor for removal and installation because wire is wound around a gear or pulley. Thus, running cost and maintenance cost increase.

Second, the control accuracy of the articulation or the gripping portion has a limitation because wire is elongated or contracted. Further, wire has such a demerit that it can transmit a drive power only in one direction (pulling direction).

Third, there is a problem that wire is difficult to sterilize and clean. Thus, in the conventional manipulator with multiple degrees of freedom, its sterilization and cleaning before and after surgery are very complicated.

SUMMARY OF THE INVENTION

The present invention has been achieved in views of the above-described problems and an object of the invention is to provide a manipulator with multiple degrees of freedom for surgery having an excellent durability.

Another object of the present invention is to provide a manipulator with multiple degrees of freedom for surgery and controllable at a high precision.

Still another object of the present invention is to provide a manipulator with multiple degrees of freedom for surgery and easy to sterilize and clean.

The present invention concerns a manipulator with multiple degrees of freedom which is driven by a driving means. More particularly, it concerns a manipulator with multiple degrees of freedom used for minimally invasive surgery such as abdominal cavity surgery. As the driving means, a drive unit including a reciprocatory output axis, for example, an actuator may be used.

The manipulator with multiple degrees of freedom of the present invention includes at least three degrees of freedom including relative opening/closing of a pair of gripping members, rotation of both the gripping members around a first axis and rotation of both the gripping members around a second axis existing on an imaginary plane substantially perpendicular to the first axis. The drive power from the driving means is converted to each motion of the opening/closing of the gripping members, rotation thereof around the first axis and rotation thereof around the second axis, by a link mechanism.

Thus, the present invention can abolish wire which is a conventional ordinary means because the drive power transmitting means is constituted of link mechanism (system in which a plurality of links (rigid body) are connected in pair).

Thus, the present invention has following advantages as compared with the conventional technology of wire drive. The link mechanism cannot be elongated or broken unlike wire because the link mechanism has a high stiffness. Thus, the durability can be improved thereby minimizing the frequency of replacement of the manipulator. Further, the control accuracy and gripping force of the gripping member and rotary portion can be increased because link mechanism is never elongated or contracted unlike wire. Further, the link mechanism is easy to sterilize and clean. Additionally, attachment and detachment between the manipulator and driving means can be simplified or facilitated because the link does not need to be wound around a gear or pulley unlike wire.

An aspect of the manipulator with multiple degrees of freedom of the present invention comprises: a pair of gripping members; a first axis that connects both the gripping members rotatably; a second axis existing on an imaginary plane perpendicular to the first axis; a first link mechanism for converting a drive power of the driving means to a rotary motion of one gripping member around the first axis; a second link mechanism for converting a drive power of the drive means to a rotary motion of the other gripping member around the first axis; and a third link mechanism for converting a drive power of the driving means to a rotary motion of both the gripping members around the second axis.

Under this aspect, if the first and second link mechanisms are controlled to equalize the rotation amount of both the gripping members, the both gripping members rotate with an opening degree and if the first and second link mechanism are controlled to make the rotation amount of both the gripping members different from each other, both the gripping members carry out relatively opening/closing motion. That is, the opening/closing motion of the gripping members and the rotation motion around the first axis are achieved using the common axis (the first axis) and link mechanisms (the first and second link mechanisms). Thus, reduction in the quantity and size of components of the manipulator can be achieved.

Preferably, the manipulator with multiple degrees of freedom further comprises: a first supporting body (or a first supporting means) for supporting the gripping members with the first axis; and a second supporting body (or a second supporting means) for supporting the first supporting body with the second axis. In the meantime, the first and second axes may be an independent member or a portion like a protrusion formed integrally on the gripping member or the supporting body.

Preferably, each of the first and second link mechanisms comprises: a first link supported slidably by the first supporting body; a second link supported slidably by the second supporting body; and a third link for connecting between the first link and the second link. At this time, preferably, the first link and third link and the second link and third link are connected through a turning pair and the rotary axes of that turning pair and the second axis are provided in parallel.

The stability of the motion is increased and the transmission loss of a drive power is reduced because the first and second links are supported slidably by the supporting body. Because the first link is supported by the same first supporting body as for the first axis (the gripping member), a positional relationship between the sliding direction of the first link and the axial direction of the first axis is always kept constant even if the first supporting body rotates around the second axis, thereby improving the stability of motion of the gripping member.

Even under a condition in which the other motions than a motion in the sliding direction are restrained, the first link and second link can be located at an appropriate positional relation depending on a rotation angle of the first supporting body because the third link exists. Further, in a condition in which the first supporting body is bent, that is, the sliding directions of the first link and second link are unparallel, the reciprocating motion of the second link is converted in its direction through the third link and transmitted to the first link.

It is preferable to provide a connecting link for connecting between the first link and the gripping member. As a result, the reciprocating motion of the first link can be converted to a rotary motion of the gripping member.

Preferably, the dimensions and relative arrangement of respective components are set up so that the axial line of the second axis is perpendicular to the third link when the first link, second link and third link are arranged in line.

With this structure, an intersection between a virtual extension stretched from an end on the third link side of the first link and a virtual extension stretched from an end on the third link side of the second link comes to exist on the axial line of the second axis when the first supporting body is bent as well as when the first to third links are arranged in line. In other words, when the first supporting body is bent, the first link and third link always rotate in the same direction with respect to the second link. As a consequence, the rotary motion of the first supporting body and the motion of the first and second link mechanisms are stabilized.

More preferably, the rotation range of the gripping members is predetermined and the axial line of the second axis and the third link are set to be always perpendicular to each other in the rotation range when the first link, second link and third link slide with a condition in which they are arranged in line.

With this structure, when the first supporting body is bent, the first link and the third link always rotate in the same direction with respect to the second link even if the first supporting body and the gripping member are in any condition, thereby the rotary motion of the first supporting body and the motion of the first and second link mechanisms being stabilized more.

"The condition in which they are arranged in line" refers to a condition in which respective line segments are arranged on the same line when a model is virtually considered by the first to third links are replaced with the respective line segments. That is, although the links as a specific component has a thickness, width or nonlinear shape, they can be grasped just in mechanical terms without being gripped by such design matters. Regarding a perpendicularity between the axial line of the second axis and the third link, the third link is replaced with a virtual line segment upon consideration. The perpendicularity of lines (line segments) refers to intersection of both the lines (line segments) at right angle on the same plane and does not include a case where they are in a skew state.

Preferably, the third link mechanism comprises: a fourth link supported slidably by the second supporting body; a fifth link that is fixed to the first supporting body and rotatable around the second axis; and a sixth link for connecting between the fourth link and the fifth link.

As a consequence, the reciprocating motion of the fourth link is converted to a rotary motion of the fifth link by the sixth link. The stability of the motion is increased and the transmission loss of a drive power is reduced because the fourth link is supported slidably by the second supporting body.

The present invention enables the durability and control accuracy to be raised by employing a link mechanism as a drive power transmitting means. Further, the present invention facilitates sterilization, cleaning and attachment/detachment to/from a driving means.

BRIEF DESCRIPTION OF THE DRAWINGS

FIG. 5 is a diagram showing an action of a first link mechanism.

FIG. 6 is a diagram showing an action of the first link mechanism.

DETAILED DESCRIPTION OF THE PREFERRED EMBODIMENTS

Hereinafter, preferred embodiments (implementations) of the present invention will be described in detail by way of example with reference to accompanying drawings.

(Configuration of Bending Forceps System)

Figure 1:
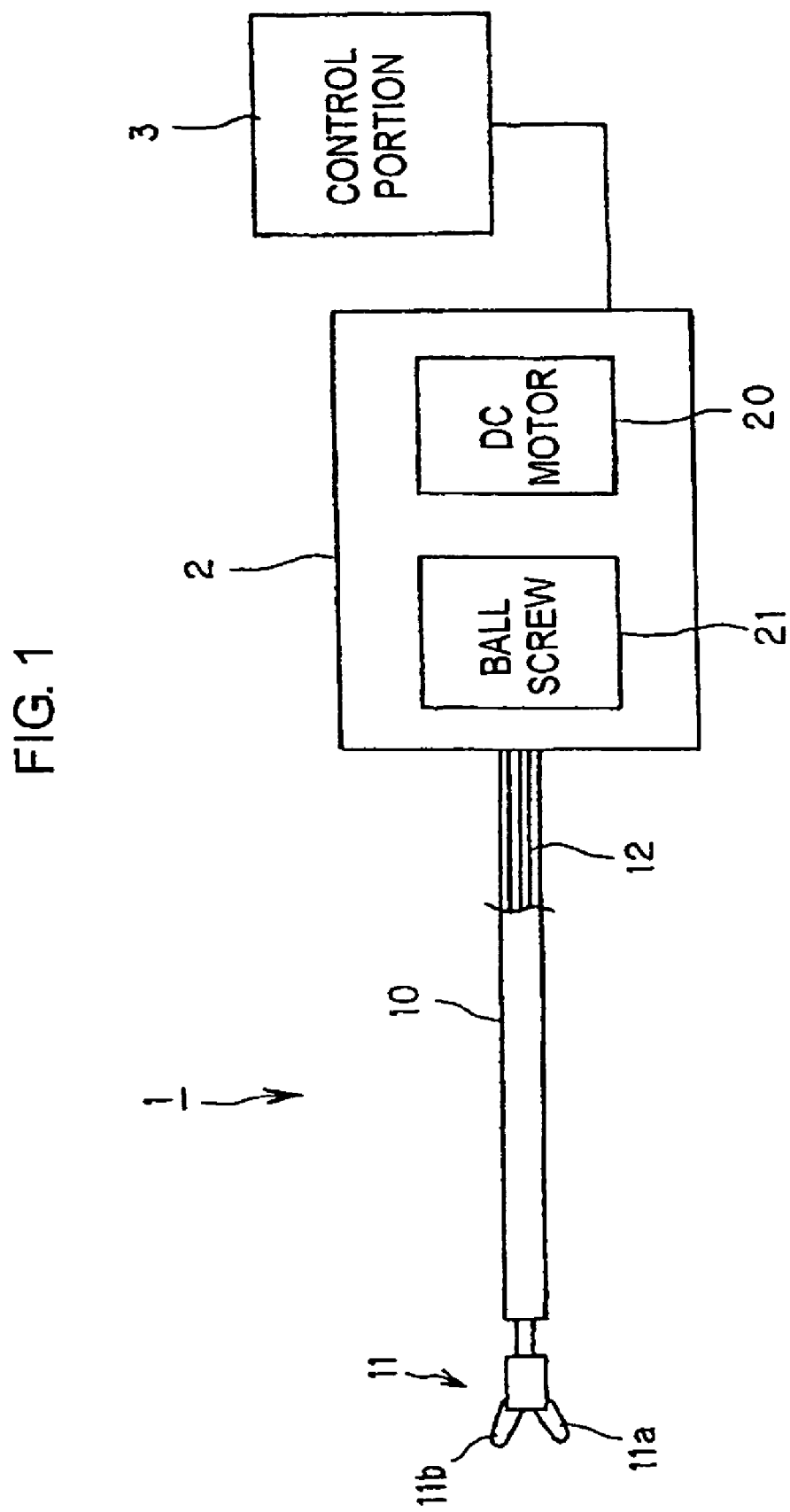
FIG. 1 is a diagram showing a bending forceps system including a manipulator with multiple degrees of freedom (bending forceps) according to an implementation of the present invention.

FIG. 1 shows a bending forceps system including a manipulator with multiple degrees of freedom according to an implementation of the present invention.

The bending forceps system comprises a bending forceps 1 which is a manipulator with multiple degrees of freedom, an actuator 2 which is a driving means for driving the bending forceps 1 and a control portion 3 for controlling the actuator 2. This bending forceps system is used for minimally invasive surgery such as abdominal cavity surgery and the like.

The bending forceps 1 generally comprises an arm portion 10 to be attached to the actuator 2 and a gripping portion 11 provided at the front end of the arm portion 10. The gripping portion 11 is provided with a pair of gripping members 11a, 11b which can be opened/closed freely. The gripping portion 11 has three degrees of freedom of bending (rotation) having two degrees of freedom and opening/closing of the gripping members 11a, 11b. The motion of three degrees of freedom is achieved when a drive power of the actuator 2 is transmitted through three input axes 12 inserted through the arm portion 10.

The actuator 2 has a DC motor 20, a ball screw 21 and the like. A drive power (rotary motion) generated by the DC motor 20 is transmitted to the ball screw 21 through a belt and a pulley and converted to reciprocating motion. The output axis of the ball screw 21 is connected to the input axis 12 of the bending forceps 1.

The control portion 3 is constituted of, for example, a computer, master robot and the like.

If an operator (surgeon) operates the master robot, its motion information is inputted to the computer. The computer generates a control signal of the DC motor 20 based on the motion information and outputs it. The DC motor 20 is rotated according to this control signal so as to give a drive power in a pushing direction or pulling direction to each input axis 12 of the bending forceps 1 via the ball screw 21. As a consequence, the gripping portion 11 at the front end of the bending forceps 1 is bent and opened/closed to achieve a desired motion.

(Structure of Bending Forceps)

Figure 2:
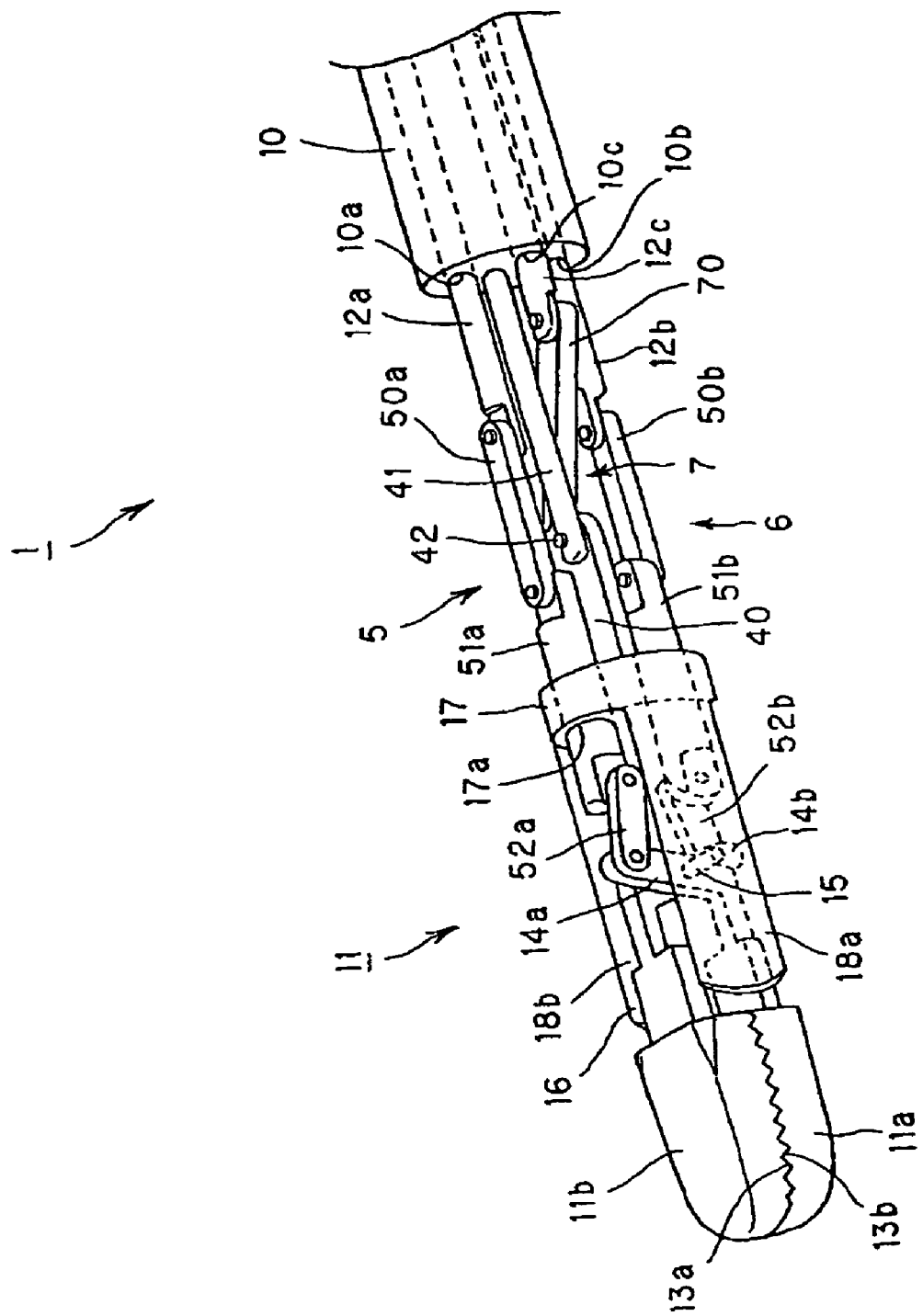
FIG. 2 is a perspective view of the front end portion of the bending forceps.
Figure 3:
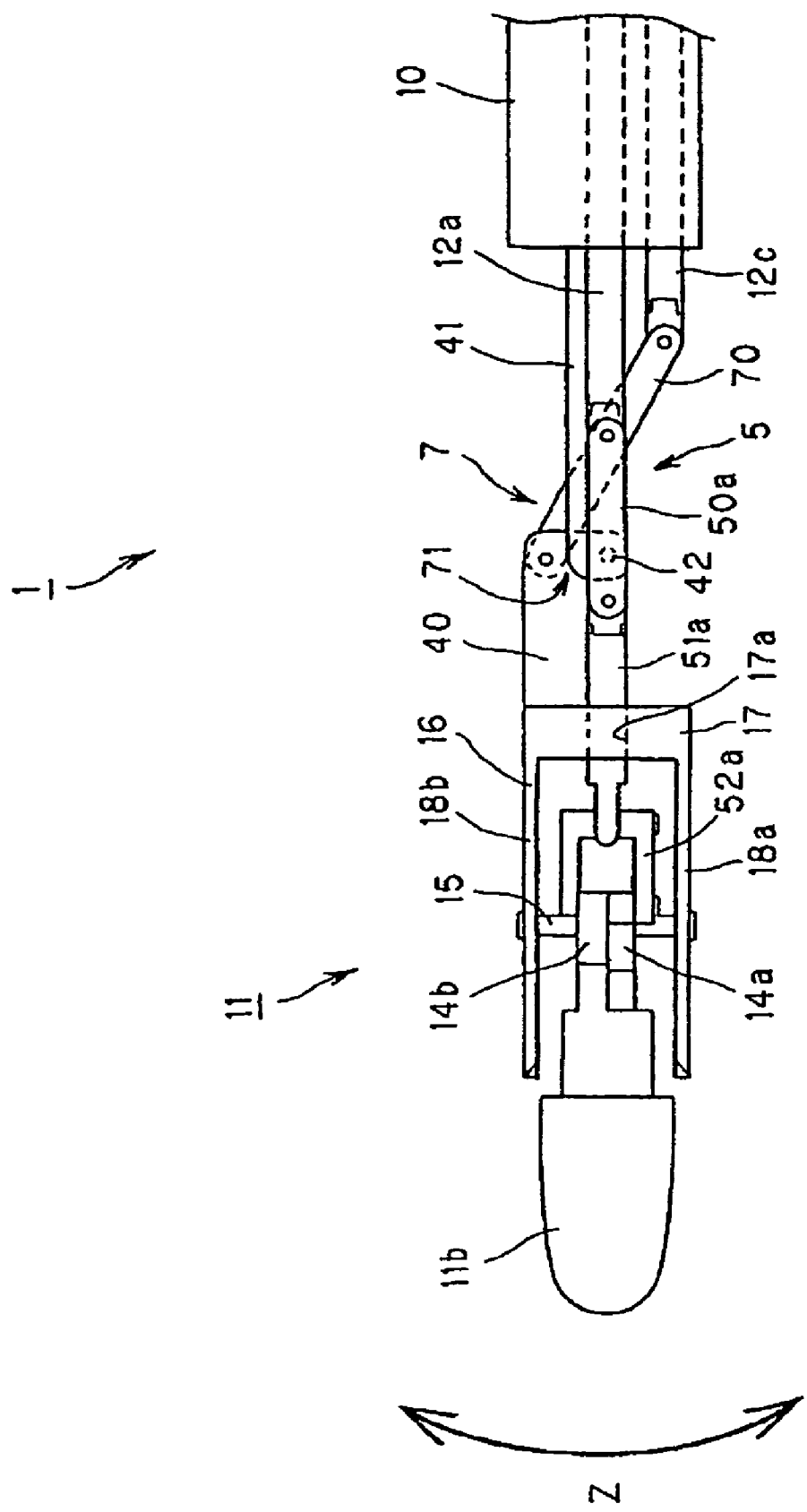
FIG. 3 is a top view of the front end portion of the bending forceps.
Figure 4:
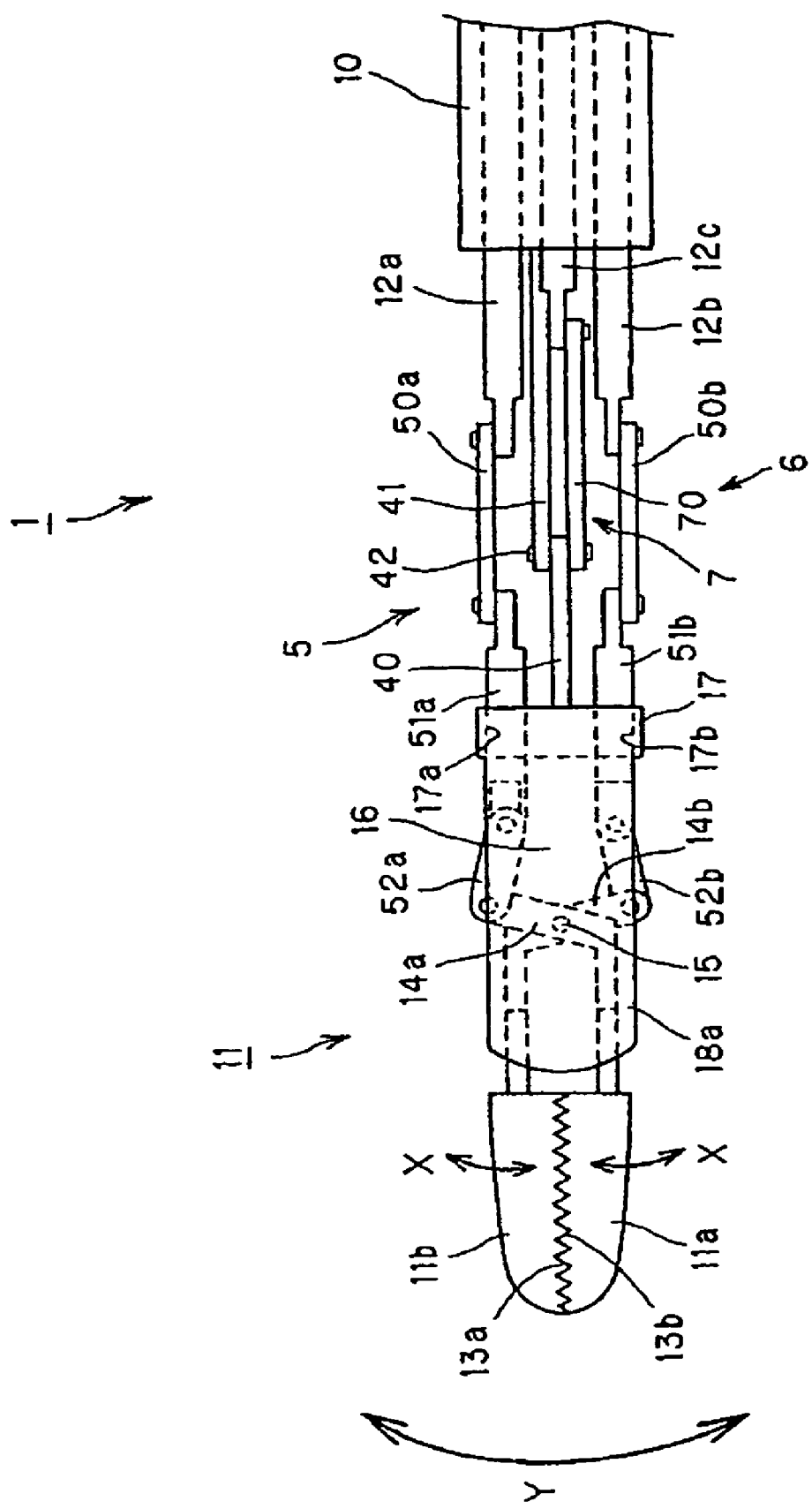
FIG. 4 is a side view of the front end portion of the bending forceps.

Next, the structure of the bending forceps 1 will be described in detail with reference to FIGS. 2 to 4. FIG. 2 is a perspective view of the front end portion of the bending forceps 1. FIG. 3 is a top view and FIG. 4 is a side view thereof.

As shown in these Figures, a pair of the gripping members 11a, 11b, are provided at the front end of the gripping portion 11 of the bending forceps 1. The gripping member 11a and the gripping member 11b have a substantially symmetrical shape and each have gripping teeth 13a, 13b which mesh with each other at their matching face (gripping face). The proximal ends of the gripping members 11a, 11b are bent inwardly into an L shape so as to form link portions 14a, 14b. Both the gripping members 11a, 11b are connected to be rotatable freely by a first axis 15 at an intersecting portion between the link portions 14a and 14b. In the meantime, the axial line of the first axis 15 is located on the same plane as the gripping face.

This first axis 15 is supported by a first supporting body 16. The first supporting body 16 is a substantially U-shaped member comprising a disc-like base portion 17 and two side wall portions 18a, 18b erected in the direction of the gripping members 11a, 11b from both side ends of this base portion 17. The side wall portions 18a, 18b are extended to a position where they cover the proximal end portion of the gripping members 11a, 11b and the first axis 15 is supported between the sidewall portion 18a and the side wall portion 18b.

A link portion 40 extending to the arm portion (second supporting body) 10 is provided on the base portion 17 of the first supporting body 16. A fixed link 41 extending to the first supporting body 16 is provided on an end face of the arm portion 10. The link portion 40 of the first supporting body 16 and the fixed link 41 of the arm portion 10 are connected rotatably with a second axis 42. The second axis 42 is provided to exist on an imaginary plane substantially perpendicular to the first axis 15.

With the above-described structure, the bending forceps 1 has three degrees of freedom of a relative opening/closing (arrow X) of the gripping members 11a, 11b (around the first axis 15), a rotation (arrow Y) of both the gripping members 11a, 11b around the first axis 15 and a rotation (arrow Z) of both the gripping members 11a, 11b around the second axis 42. Because the bending forceps 1 itself is rotatable around its central axis and the bending forceps system is entirely movable in three dimensions, the freedom of the entire system is seven degrees of freedom.

(Link Mechanism)

In this implementation, all the means for transmitting a drive power from the actuator 2 to the gripping portion 11 is constituted of link mechanism. That is, a drive power (reciprocating motion) inputted from the actuator 2 to an input axis 12 (12a, 12b, 12c) is converted by a link mechanism to respective motions including opening/closing of the gripping members 11a, 11b, rotation about the first axis 15 and rotation about the second axis 42. Hereinafter, the specific structure of the link mechanism will be described in detail.

The bending forceps 1 has three link mechanisms including a first link mechanism 5, a second link mechanism 6 and a third link mechanism 7. The first link mechanism 5 converts a drive power of the actuator 2 to a rotary motion of one gripping member 11a around the first axis 15 and the second link mechanism 6 converts a drive power of the actuator 2 to a rotary motion of the other gripping member 11b around the first axis 15. Further, the third link mechanism 7 converts a drive power of the actuator 2 to a rotary motion of the first supporting body 16 (both gripping members 11a, 11b) around the second axis 42.

<First and Second Link Mechanisms>

The first link mechanism 5 is constituted of four links including the input axis (second link) 12a, a connecting link (third link) 50a, restraint link (first link) 51a and connecting link 52a in order from the arm portion 10 side. The input axis 12a and the connecting link 50a are connected with a pin and the connecting link 50a and the restraint link 51a are connected with a pin and these pins are provided in parallel to the second axis 42. The restraint link 51a and the connecting link 52a are connected with a pin and the connecting link 52a and the link portion 14a of the gripping member 11a are connected with a pin. These pins are provided in parallel to the first axis 15.

The second link mechanism 6 is constituted of four links including the input axis (second link) 12b, a connecting link (third link) 50b, restraint link (first link) 51b and connecting link 52b in order from the arm portion 10 side. Because the second link mechanism 6 is a mechanism symmetrical to the first link mechanism 5, only the first link mechanism 5 will be described.

The restraint link 51a is inserted through a slide hole 17a provided in the base portion 17 of the first supporting body 16. As a consequence, the restraint link 51a is slidable with respect to the first supporting body 16 while other motions than that in the sliding direction are restrained.

The input axis 12a is inserted into a slide hole 10a provided in an end face of the arm portion 10 which is a second supporting body. As a consequence, the input axis 12a becomes slidable with respect to the arm portion 10 while other motions than that in the sliding direction are restrained.

When in the first link mechanism 5, a drive power in the pushing direction is inputted to the input axis 12a from a state shown in FIG. 5: (a), the drive power is transmitted to the restraint link 51a through the connecting link 50a so that the restraint link 51a slides in the left direction in the same Figure. Then, the sliding motion of the restraint link 51a is converted to a rotary motion of the link portion 14a around the first axis 15 through the connecting link 52a. As a consequence, the gripping member 11a is rotated as shown in FIG. 5: (b).

Conversely, if a drive power in the pulling direction is inputted to the input axis 12a in the state shown in FIG. 5: (a), the restraint link 51a slides in the right direction of the same Figure. Then, because that sliding motion is converted to a rotary motion around the first axis 15 of the link portion 14a by the connecting link 52a, the gripping member 11a is rotated as shown in FIG. 5: (c).

In this implementation, the dimensions and relative arrangement of the input axis 12a, the connecting link 50a and the restraint link 51a are set to satisfy a following condition.

First, the rotation range of the gripping member 11a is determined. This rotation range is determined appropriately depending on both mechanical restrictions (singular points and avoidance of interference between components) and operational requirements. Here, it is assumed that the states of FIG. 5: (b) to (c) are set as a rotation range.

When the input axis 12a, the connecting link 50a and the restraint link 51a slide with a state in which they are arranged in line, the axial line of the second axis 42 is always perpendicular to the connecting link 50a in the above-described rotation range. In other words, the pins on both ends of the connecting link 50a are set to a position in which they stride over the second axis 42 in any case of FIG. 5: (a) to (c).

If such a condition is satisfied, an intersection 55 between a virtual extension 53 from an end of the restraint link 51a and a virtual extension 54 from an end of the input axis 12a exists on the axial line of the second axis 42 when the first supporting body 16 is bent as shown in FIG. 6: (b) and (c) as well as when the three links are arranged in line as shown in FIG. 6: (a). That is, even if the first supporting body 16 is bent in any direction, the restraint link 51a and the connecting link 50a always rotate in the same direction as viewed from the input axis 12a.

If the restraint link 51a and the connecting link 50a are rotated in the same direction, the internal angles between the restraint link 51a, the connecting link 50a, and input axis 12a can be set large because the rotation angle θ of the first supporting body 16 is divided to a rotation angle α of the restraint link 51a and a rotation angle β of the connecting link 50a. Thus, even if the first supporting body 16 is bent, transmission loss of the drive power is small thereby achieving a stable link motion and enabling the gripping member 11a to rotate smoothly.

A mechanical property that the restraint link 51a and the connecting link 50a always rotate in the same direction can eliminate such a singular point that the restraint link 51a and the connecting link 50a may fall in different directions, which is an advantage.

The second link mechanism 6 executes the same motion as the above-described first link mechanism 5 although description thereof is omitted here. Thus, both the gripping members 11a, 11b rotate with an opening degree if the first and second link mechanisms 5, 6 are controlled so as to equalize the rotation amounts of both the gripping members 11a, 11b and both the gripping members 11a, 11b relatively execute opening/closing motion if the first and second link mechanisms 5, 6 are controlled so as to make the rotation amounts of the gripping members 11a, 11b different from each other.

According to this implementation, motions of two degrees of freedom of the opening/closing of the gripping members 11a, 11b and a rotation around the first axis 15 are achieved with the common axis (first axis 15) and link mechanism (first and second link mechanisms 5, 6) so as to reduce the quantity of components of the bending forceps 1 and the size thereof.

<Third Link Mechanism>

Figure 7:
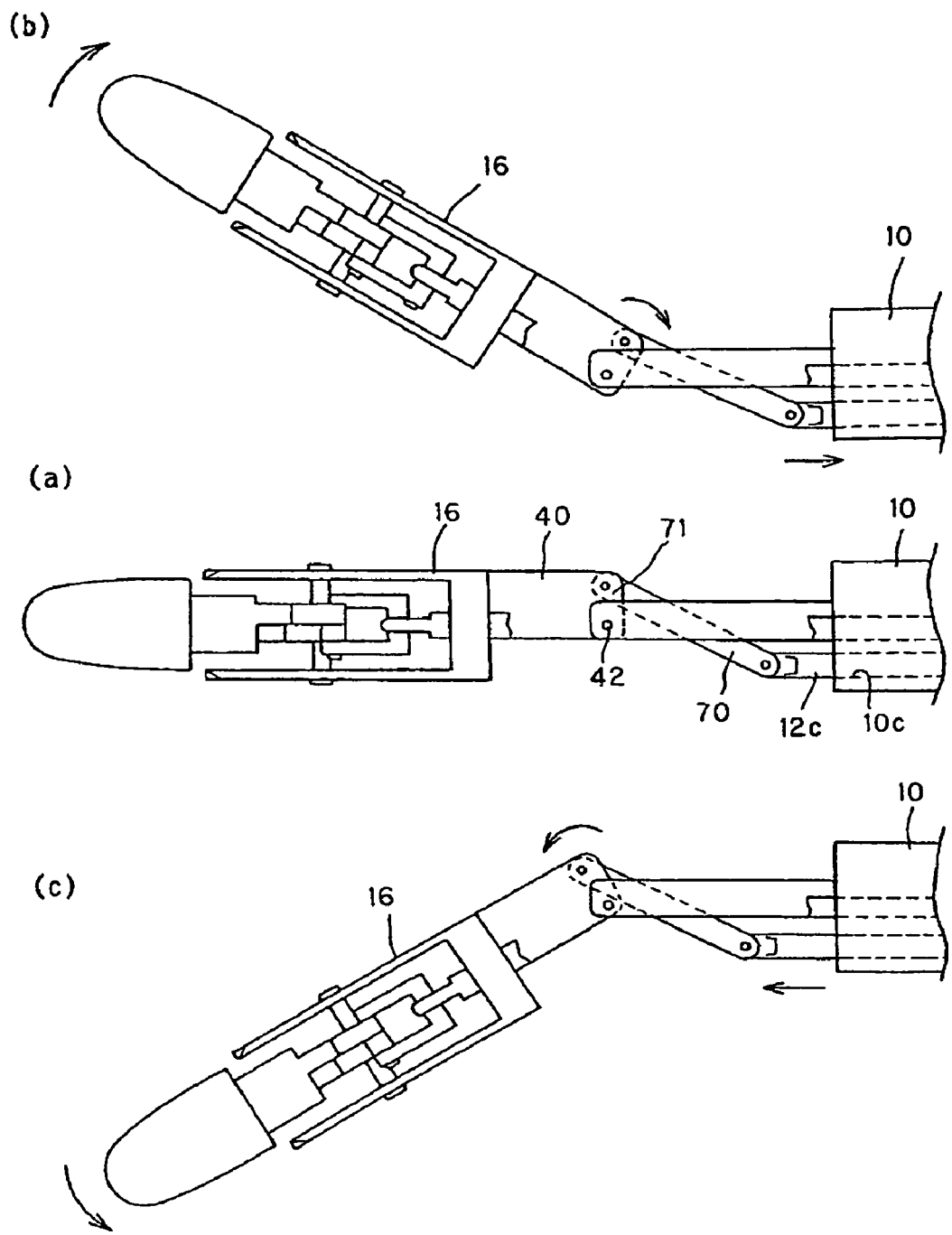
FIG. 7 is a diagram showing an action of a third link mechanism.

As shown in FIG. 7: (a), the third link mechanism 7 is constituted of three links, input axis (fourth link) 12c, connecting link (sixth link) 70 and crank (fifth link) 71 in order from the arm portion 10 side. The crank 71 of this implementation is formed integrally on the link portion 40 of the first supporting body 16. As a result of such formation, the crank 71 is fixed to the first supporting body 16 and rotatable about the second axis 42. The input axis 12c and the connecting link 70 are connected with a pin and the connecting link 70 and the crank 71 are connected with a pin and these pins are provided in parallel to the second axis 42.

The input axis 12c is inserted through a slide hole 10c provided in the end face of the arm portion 10 which is a second supporting body. As a consequence, the input axis 12c is slidable with respect to the arm portion 10 while other motions than the one in the sliding direction are restrained. Because according to this implementation, an area in which the input axis 12c reciprocates and an area in which the crank 71 rotates are disposed on opposite sides with respect to the second axis 42, a state (singular point) in which the input axis 12c and the connecting link 70 are arranged in line can be avoided.

If a drive power in the pushing direction is inputted to the input axis 12c from a state of FIG. 7: (a) in the third link mechanism 7, its sliding motion is converted to a rotary motion of the crank 71 through the connecting link 70. As a consequence, the first supporting body 16 rotates as shown in FIG. 7: (c).

Conversely, if a drive power in the pulling direction is inputted to the input axis 12c in the state shown in FIG. 7: (a), its sliding motion is converted to a rotary motion of the crank 71 by the connecting link 70, so that the first supporting body 16 rotates as shown in FIG. 7: (b).

Because a state in which the connecting link 70 and the crank 71 are disposed in line becomes a singular point, the rotation range of the first supporting body 16 is preferably set inside of that state.

Because the drive power transmitting means for converting the drive power of the actuator 2 to respective motions of two degrees of freedom of bending (rotation) and opening/closing of the gripping portion 11 is achieved with the link mechanism, wire which is a conventional ordinary means can be abolished.

The link mechanism is never elongated or broken unlike wire because it has a high stiffness. Thus, its durability can be increased so that the frequency of replacement of the bending forceps 1 can be reduced as much as possible. Further, because the link mechanism is never elongated or contracted unlike wire, control accuracy of the gripping member and rotary portion and gripping force can be increased. The link mechanism allows sterilization and cleaning to be carried out easily. Further, attachment and detachment of the bending forceps 1 and actuator 2 (that is, attachment and detachment of respective input axes 12*a*, 12*b*, 12*c* of the bending forceps 1 and respective output axes of the actuator 2) can be simplified and facilitated because the link does not need to be wound around a gear or pulley unlike wire.

In the meantime, the above-described implementation is just an exemplification of an implementation of the present invention. The present invention is not restricted to the above-described implementations but may be modified in various ways within a scope of technical philosophy thereof.

DESCRIPTION OF REFERENCE NUMERALS

1: Bending forceps (manipulator with multiple degrees of freedom)
2: Actuator (driving means)
3: Control portion
5: First link mechanism
6: Second link mechanism
7: Third link mechanism
10: Arm portion (second supporting body)
10*a*, 10*b*, 10*c*: Slide hole
11: Gripping portion
11*a*, 11*b*: Gripping member
12: Input axis
12*a*, 12*b*: Input axis (second link)
12*c*: Input axis (fourth link)
13*a*, 13*b*: Gripping tooth
14*a*, 14*b*: Link portion
15: First axis
16: First supporting body
17: Base portion
17*a*, 17*b*: Slide hole
18*a*, 18*b*: Side wall portion
20: DC motor
21: Ball screw
40: Link portion
41: Fixed link
42: Second axis
50*a*, 50*b*: Connecting link (third link)
51*a*, 51*b*: Restraint link (first link)
52*a*, 52*b*: Connecting link
53: Extension
55: Intersection
70: Connecting link (sixth link)
71: Crank (fifth link)

The invention claimed is:

1. A manipulator with multiple degrees of freedom for surgery driven by a driving means, comprising:
a pair of gripping members;
a first axis that connects both the gripping members rotatably;
a second axis existing on an imaginary plane substantially perpendicular to the first axis;
a first link mechanism for converting a drive power of the driving means to a rotary motion of one gripping member around the first axis;
a second link mechanism for converting a drive power of the driving means to a rotary motion of the other gripping member around the first axis;
a third link mechanism for converting a drive power of the driving means to a rotary motion of both the gripping members around the second axis;
a first supporting body for supporting the gripping members with the first axis; and
a second supporting body for supporting the first supporting body with the second axis,
wherein each of the first and second link mechanisms comprises: a first link supported slidably by the first supporting body, a second link supported slidably by the second supporting body; and a third link for connecting between the first link and the second link, and
wherein each of the link mechanisms is a mechanism in which a plurality of links are connected in pairs.

2. A manipulator with multiple degrees of freedom according to claim 1 wherein an axial line of the second axis and the third link are perpendicular to each other when the first link, the second link and the third link are arranged in line.

3. A manipulator with multiple degrees of freedom according to claim 2 wherein a rotation range of the gripping member is predetermined and when the first link, the second link and the third link slide with a state in which they are arranged in line, the axial line of the second axis and the third link are always perpendicular to each other in the rotation range.

4. A manipulator with multiple degrees of freedom according to any one of claims 1, 2 and 3, wherein the third link mechanism comprises:
a fourth link supported slidably by the second supporting body;
a fifth link that is fixed to the first supporting body and rotatable around the second axis; and
a sixth link for connecting between the fourth link and the fifth link.

* * * * *